(12) United States Patent
Bernardelli

(10) Patent No.: US 6,878,821 B2
(45) Date of Patent: Apr. 12, 2005

(54) MODIFYING CHEMOSELECTIVITY DURING OXIDATION OF NITROGEN COMPOUNDS

(75) Inventor: Patrick Bernardelli, Fontenay-aux-roses (FR)

(73) Assignee: Warner-Lambert LLC, Morris Plains, NJ (US)

( * ) Notice: Subject to any disclaimer, the term of this patent is extended or adjusted under 35 U.S.C. 154(b) by 8 days.

(21) Appl. No.: 10/240,364

(22) PCT Filed: Mar. 22, 2001

(86) PCT No.: PCT/EP01/03635
§ 371 (c)(1), (2), (4) Date: Feb. 27, 2003

(87) PCT Pub. No.: WO01/72667
PCT Pub. Date: Oct. 4, 2001

(65) Prior Publication Data
US 2003/0176723 A1 Sep. 18, 2003

(30) Foreign Application Priority Data
Mar. 29, 2000 (FR) .............................. 00 03991

(51) Int. Cl.$^7$ ............................................. C07D 243/14
(52) U.S. Cl. ...................................................... 540/570
(58) Field of Search .......................... 540/570; 564/298, 564/299, 324

(56) References Cited

U.S. PATENT DOCUMENTS 3,901,879 A * 8/1975 Coffen et al. ............... 260/239
5,760,216 A * 6/1998 Chorghade et al. ......... 540/145
6,103,892 A * 8/2000 Breslow et al. .............. 536/46

FOREIGN PATENT DOCUMENTS

| WO | WO9608455 | 3/1996 | ........... C07B/33/00 |
| WO | WO0110797 | 2/2001 | ........... C07B/33/00 |

OTHER PUBLICATIONS

Ganem et al, "A Biomimetic Oxidation" Tetrahedron Letters, vol. 21, pp. 689–690 (1980).*
Dodd and Hyaric, "The Oxidation of Aromatic Aldehydes to Carboxylic Acids Using Hydrogen Peroxide in Formic Acid" Synthesis, vol. 3, pp. 295–297 (1993).*
Ravikumar et al, "Role of Hexafluoro–2–propanol in Selective Oxidation of Sulfide to Sulfoxide: Efficient Preparation of Glycosyl Sulfoxides" European Journal of Organic Chemistry, pp. 2937–2940 (1998).*
Morgan and Kopp, "Solvent Effects on the Stability of Simple Secondary Amides" J. Chem. Soc., Perkin Trans. 2, pp. 2759–2763 (1998).*
Kunitomo, et al., Chem. Pharm. Bull. 29(8), 251–2253, 1981.
Abraham, Michael H., *Scales of Solute Hydrogen–bonding: Their Construction and Application to Physicochemical and Biochemical Processes*, Chemical Society Reviews, Issue 22, vol. 2, pp. 73–83, (1993).

* cited by examiner

*Primary Examiner*—Richard L. Raymond
*Assistant Examiner*—Zachary C. Tucker
(74) *Attorney, Agent, or Firm*—Peter C. Richardson; Gregg C. Benson; Robert T. Ronau

(57) ABSTRACT

The invention concerns a method for chemoselective oxidation of an organic compound comprising several potentially oxidizable groups whereof at least one is a nitrogen group. Said method is characterised in that it consists in using at least a protic solvent, which is a good donor of hydrogen bonds, enabling to limit N-oxidation.

3 Claims, 1 Drawing Sheet

MODIFYING CHEMOSELECTIVITY DURING OXIDATION OF NITROGEN COMPOUNDS

Figure 1:
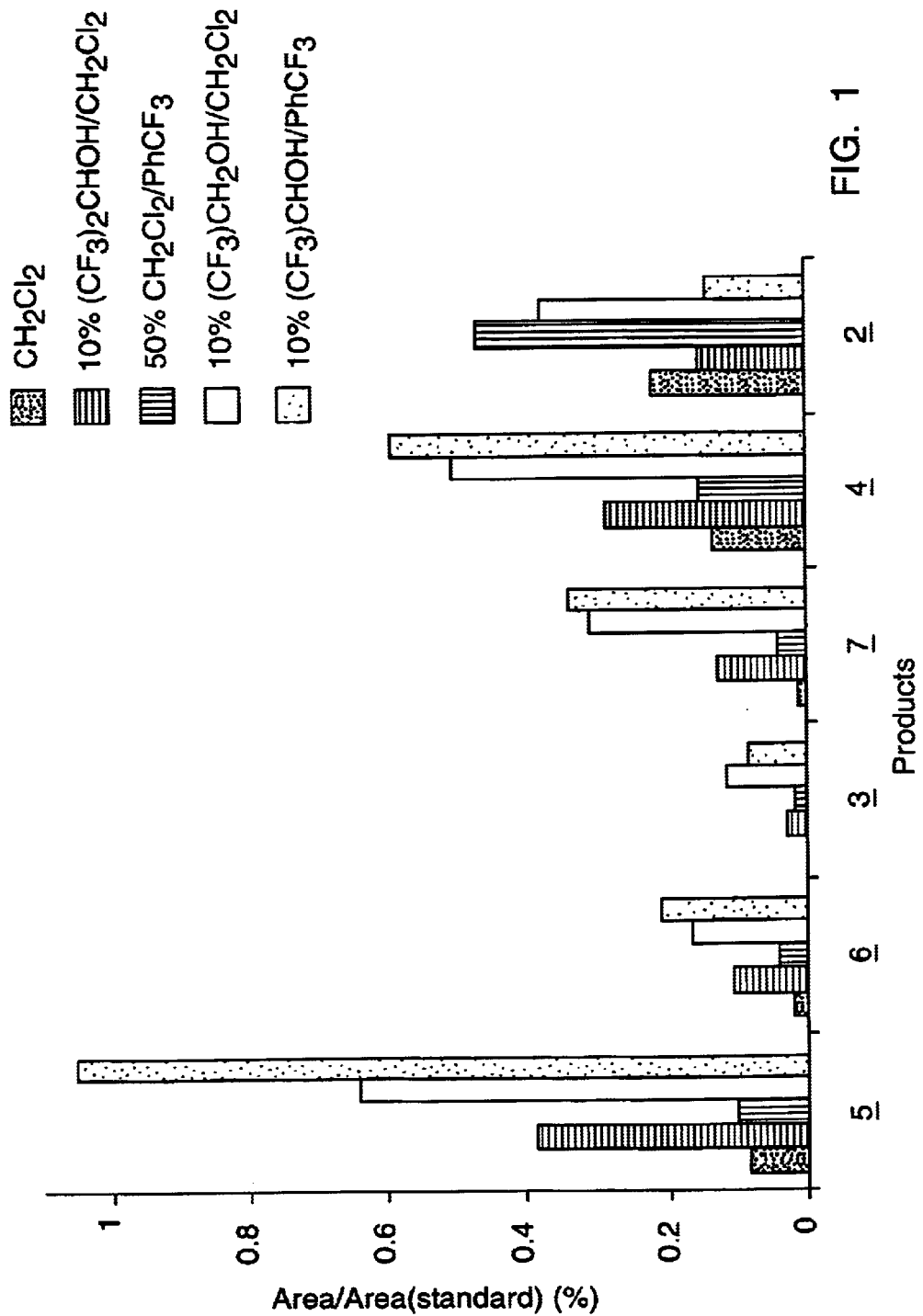

This application is the National Stage of International Application No. PCT/EP01/03635, filed Mar. 22, 2001, and claims priority from FR 00/03991, filed Mar. 29. 2000.

PRIOR ART

Metabolic studies are an important part of drug development and make it possible to predict the metabolites that will be obtained upon conversion of a given compound by body enzymes. P450 cytochromes, the main enzymes involved in the bioconversion of drugs, catalyze oxidation reactions. From an economic point of view, it is of great interest to try to predict, in vitro, the metabolites which will result from the bioconversion of a compound. For example, many drugs contain nitrogen-containing groups which may be metabolized to N-oxidized derivatives by these monooxygenase enzymes. In general, these N-oxidized products can readily be synthesized by conventional oxidation methods (e.g., reaction with peracids). In contrast to N-oxidized products, other oxidation products such as products of hydroxylation are difficult to synthesize from the starting material.

Use of metalloporphyrines to catalyze the oxidation of organic compounds, as described in patent application PCT 96/08455, makes it possible to mimic the oxidation reactions which take place in biological systems, and to prepare the potential metabolites resulting, among other things, from the N-oxidation and hydroxylation of the starting material. However, because of their nonbinding doublet, nitrogen-containing groups are rich in electrons and hence are generally more reactive under oxidation conditions than are carbon-hydrogen bonds.

During oxidation reactions one can obtain satisfactory results of hydroxylation of the starting material by using a salt of the starting material or by carrying out the reaction in a strongly acid medium (by adding to the reaction medium strong Brönsted acids such as hydrochloric or trifluoroacetic acid). The presence of these strong Brönsted acids brings about complete protonation of the nitrogen-containing groups of the organic compound to be oxidized. Nevertheless the salts of corresponding nitrogen-containing compounds are not always stable in the reaction medium, and/or the presence of a strong Brönsted acid in the medium can be harmful to the starting material and/or to the oxidation products.

SUMMARY OF THE INVENTION

The invention makes it possible to solve this technical problem by employing a process carried out under mild conditions and using a protic solvent or co-solvent whose properties permit orienting the chemoselectivity of the oxidation reaction.

In particular, the invention makes it possible to avoid the instability problems which may result from the use of salts of the compound to be oxidized, and also to avoid racemization and/or degradation of the starting materials and/or of the oxidation products and/or of the reagents, drawbacks which characterize the use of strong acids.

Hence the present invention relates to a process of chemoselective oxidation of an organic compound having several oxidizable groups, at least one of which is a nitrogen-containing group. The process consists in contacting an organic compound to be oxidized with a reaction mixture comprising an oxidizing agent in a protic solvent which is a good donor of hydrogen bonds, and is optionally accompanied by an inert aprotic solvent. The protic solvent is capable of forming a hydrogen bond with a nitrogen-containing group of the compound to be oxidized, thus limiting the oxidation of this nitrogen-containing group, thereby favoring the oxidation of other functional groups of the compound to be oxidized. The process then consists in recovering the products resulting from the oxidation reaction.

The present invention also relates to a process of chemoselective oxidation of an organic compound having several oxidizable groups, at least one of which is a nitrogen-containing group. The process consists in contacting said organic compound with a reaction mixture comprising an oxidizing agent and a protic solvent. The protic solvent is capable, in said reaction medium, of forming a hydrogen bond with one or several nitrogen-containing groups of said organic compound, without leading to complete protonation of said nitrogen-containing group or groups, thereby favoring the oxidation of other functional groups of the compound to be oxidized. The process then consists in recovering the products resulting from the oxidation reaction.

The process of the invention may be used in metabolic studies. In effect it makes it possible to change the proportion of the different products obtained at the end of the oxidation of an organic compound whose potential metabolites the researchers wish to know, and in particular, to increase the yield of oxidation products that are difficult to obtain under conventional oxidation conditions. It may also permit to obtain supplementary metabolites and thus change the nature of the products obtained at the end of the oxidation reaction.

BRIEF DESCRIPTION OF THE INVENTION

FIG. 1 shows the effect of different solvents or solvent mixtures on the nature and proportion of the products obtained at the end of the oxidation of N-(9-methyl-4-oxo-1-phenyl-3,4,6,7-tetrahydro-[1,4]diazepino[6,7,1-hi]indol-3-yl)isonicotinamide (1) in the presence of an oxidizing agent (iodosobenzene) and a catalyst (manganese (tetra-(2,6-dichlorophenyl)porphyrin).

DETAILED DESCRIPTION OF THE INVENTION

When an organic compound having several oxidizable groups is in a reaction medium corresponding to oxidation conditions, the different potentially oxidizable sites of said compound are in competition vis-a-vis the oxidizing agent. In that case it is the site most reactive under oxidation conditions that is mainly oxidized.

Because of their nonbinding electron doublet, nitrogen-containing compounds or groups are generally very reactive under oxidation conditions, because the latter involve electrophilic reagents. Thus when a nitrogen-containing organic compound is used as reagent in an oxidation reaction, the majority products obtained will originate from the nitrogen-containing group.

Hence the consequence of the process of the invention is to limit the oxidation of one or several nitrogen-containing groups present in the organic compound, in favor of other, less reactive functional groups present in the same organic compound.

Preferentially, the process of the invention makes it possible to obtain a proportion of N-oxidized products with respect to the total amount of products resulting from the reaction, of between 0 and 50%. More particularly, the process of the invention makes it possible to obtain a proportion of N-oxidized products with respect to the total amount of products resulting from the reaction, of between 0 and 20%, 0 and 15%, or 0 and 5%.

The present process comprises the use of an oxidizing agent and of a protic solvent that is a good donor of hydrogen bonds, and is characterized by a high α parameter. Parameters α and β make it possible, respectively, to measure the ability of a molecule to donate a hydrogen bond and the ability of a molecule to accept a hydrogen bond (for more details, see: Michael H. Abraham, Chem. Dep., Univ. Coll. London, London, UK. Chem. Soc. Rev. (1993), 22(2), 73-83). Such a solvent, having a high α parameter, may form a complex, within the starting material, with the functional group having the highest β parameter, that is one being the best hydrogen bond acceptor. A hydrogen bond is thus formed between the nitrogen-containing group or groups whose oxidation is to be limited (this type of group generally has a high β parameter) and the protic solvent used. Formation of this bond greatly decreases the reactivity of nitrogen toward the oxidizing agent and permits the oxidation of other functional groups. Thus the protic solvent is selected so that the formation of hydrogen bonds between a hydrogen of the solvent (hydrogen bond donor) and nonbinding doublet of the nitrogen (hydrogen bond acceptor) of the nitrogen-containing group of the organic compound do not lead to complete protonation of said nitrogen-containing group.

Understood by the term "complete protonation of a nitrogen-containing group" is the fact that there is only a negligible amount of non-protonated nitrogen-containing group in the reaction medium.

Thus, as mentioned above, the process of the invention makes it possible to orient the chemoselectivity of the reaction, which allows limitation of the N-oxidation of the nitrogen-containing groups present in the starting material and which thus promotes the oxidation of other functional groups of the compound to be oxidized, such as the carbon-hydrogen bonds or carbon-carbon double bonds.

This type of chemoselectivity may be called N-chemoselectivity.

The process of the invention makes it possible, for example, to promote the hydroxylation of carbon-hydrogen bonds of an organic compound having one or more nitrogen-containing groups.

The terms "nitrogen-containing group" or "nitrogen-containing compound" are used here to designate any functional group containing a nitrogen, and, more particularly, amines (primary, secondary and tertiary), amides, imines, nitriles and optionally substituted aromatic or nonaromatic heterocycles which contain at least one nitrogen atom. The organic compound to be oxidized contains one or more nitrogen-containing groups selected from the functional groups listed above. Preferably, the organic compound to be oxidized contains one nitrogen-containing group selected from the functional groups listed above.

The oxidation reaction according to the process of the invention may be carried out in the presence of a catalyst, particularly in the presence of a metalloporphyrin, a compound which makes it possible to mimic the bioconversions undergone by a drug in a biological system.

Thus, the presence of the protic compound or solvent which is a good hydrogen bond donor and very weak Brönsted acid makes it possible to vary the chemoselectivity of the oxidation reaction under conditions that are milder than those using a strong Brönsted acid or an acid having a $pK_a$ of less than 7.

In certain cases when the $pK_a$ of the protic solvent is lower than that of the conjugated acid of the oxidizable nitrogen-containing compound, the formation of a hydrogen bond between a nitrogen-containing group of the compound to be oxidized and the protic solvent may lead to protonation of the nitrogen. This protonation or ionization of the nitrogen is preferably a partial one.

Understood by the term "partial protonation" is a proportion of organic compound to be oxidized whose nitrogen-containing group or groups are protonated by the the protic solvent to an extent of less than 80%, 50%, 20%, 10% or 1% with respect to the same nonprotonated compound.

Protic Solvent or Co-Solvent

The protic solvent used in the process of the invention is capable, in the reaction medium, of forming a hydrogen bond with one or more nitrogen-containing groups of the organic compound to be oxidized, without leading to complete protonation of said nitrogen-containing group or groups.

More particularly, the protic solvent used in the process of the invention is a protic solvent that is a very weak Brönsted acid capable, in the reaction medium, of forming a hydrogen bond with one or more nitrogen-containing groups of the organic compound to be oxidized.

The term "protic solvent that is a very weak Brönsted acid" is preferably understood to designate a solvent characterized by a $pK_a$ equal to or greater than 9.

The term "protic solvent capable of forming a hydrogen bond" is understood to mean a solvent that is a good donor of hydrogen bonds. This solvent that is a good hydrogen-bond donor is advantageously characterized by a high α parameter.

Preferably, a high α parameter will be greater than 0.43. In a particularly preferred manner, a high α parameter will be equal to or greater than 0.55.

Advantageously, the protic solvent is, in addition, highly polar and/or weakly nucleophilic.

The preferred solvent is highly polar and weakly nucleophilic.

This solvent should be protic, very weakly acidic in the sense of Brönsted ($pK_a \geq 9$) and have a high α parameter, i.e., be a good hydrogen bond donor.

The following examples illustrate but do not limit the choice of protic solvent. The protic solvent may be an alcohol such as isopropanol or tert.-butyl alcohol (or 2-methylpropanol-2).

The solvent is preferably a fluorinated alcohol such as 2-fluoroethanol, 2,2,2-trifluoroethanol, 1,1,1,3,3,4,4,4,-octafluorobutanol-2,2,2,3,3,4,4,4-heptafluorobutanol-1,2,2, 3,3,3-pentafluoropropanol-1,1,1,1,3,3,3-hexafluoro-2-methylpropanol-2, or 1,1,1,3,3,3,-hexafluoropropanol-2 (or hexafluoroisopropanol). The preferred protic solvent is hexafluoroisopropanol, because it is an extremely powerful hydrogen-bond donor (very high α parameter) and a very weak hydrogen-bond acceptor. Moreover, this compound is readily eliminated at the end of reaction by evaporation under reduced pressure, since it is highly volatile (boiling point 59° C.).

The protic compound of the process of the invention can be used as the sole solvent or as co-solvent in the reaction medium.

When the protic compound is used as co-solvent, the reaction medium contains another solvent, the main inert and aprotic solvent, which reacts neither with the reactants nor with the reaction products. In that case the protic compound, thanks to its properties, also has the advantage of facilitating dissolution of the product to be oxidized in the main solvent.

The amount of protic co-solvent used generally represents 1 to 30% equivalent by volume with respect to the main solvent. Preferably, 10% are used.

When the protic compound which allows the selectivity of the reaction to be varied is used as the sole solvent without main solvent, it permits, in that case, both the dissolution of the reactants and the chemoselectivity of the oxidation reaction.

The total amount of solvent is calculated so as to obtain a solution whose concentration of starting material is between 0.05 M and 0.5 M. The concentration of starting material is preferably 0.1 M. The total amount of solvent comprises the main solvent and the protic co-solvent if the protic compound is used as co-solvent, or the protic solvent alone if the protic compound is used as the sole solvent.

The use of the protic compound as the sole solvent or co-solvent, and the amount and nature of the protic compound to be used are parameters which a person skilled in the art can easily determine by routine experimentation.

Main Solvent

When the protic compound is used as co-solvent in the reaction medium, the main solvent is so selected that it reacts neither with the starting material nor with the reaction products. An inert aprotic solvent is preferred which does not interfere with the oxidation reaction. This main solvent can itself be composed of a combination of several solvents.

The following examples illustrate but do not limit the choice of main solvent. The main solvent may be a polyhalogenated aliphatic solvent such as 1,1,2-trichloro-1,2,2-trifluoroethane or dichloromethane, a polyhalogenated organic solvent such as 1,2-dichlorobenzene, 1,2,4-trichlorobenzene, pentafluorobenzene or trifluorotoluene. Trifluorotoluene is the preferred main solvent, because it can dissolve many different organic compounds while having a low reactivity under the oxidation conditions.

Oxidizing Agent

Numerous oxidizing agents may be used in the process of the invention. In effect the nature of the oxidizing agent is not a limiting factor in the course of an oxidation reaction according to the process of the invention. Persons skilled in the art can select the appropriate oxidizing agent from the wide variety of available oxidizing agents.

The following examples illustrate but do not limit the choice of oxidizing agent. The most frequently used oxidizing agents include m-chloroperbenzoic acid, magnesium monoperoxyphthalate, dimethyldioxirane and potassium monopersulfate.

If a catalyst such as a metalloporphyrin is used in the process of the invention, the oxidizing agent many be iodosobenzene, a 30 to 45% aqueous solution of hydrogen peroxide, an anhydrous source of hydrogen peroxide such as sodium percarbonate, urea-hydrogen peroxide complex or the like, potassium monopersulfate, sodium hypochlorite, tert.-butyl hydroperoxide, cumene hydroperoxide, m-chloroperbenzoic acid, or magnesium monoperoxyphthalate. Preferred oxidizing agents include iodosobenzene, any source of hydrogen peroxide, or potassium monopersulfate.

Hydrogen peroxide is more effective in the presence of a co-catalyst such as imidazole, ammonium acetate, N-hexylimidazole, amine N-oxides, tetrabutylammonium acetate, tert.-butylpyridine, pyridine, 4-methylpyridine, and 2,4,6-trimethylpyridine. The oxidizing agents cited in the following reference may also be used in the process of the invention: "State of the art in the development of biomimetic oxidation catalysts" by A. M. A Rocha Gonsalves and M. M. Pereira, J. Mol. Catal. A: Chem. 1996, 113, 209.

Metalloporphyrins

Synthetic metalloporphyrins are described in the international patent application WO 96/08455. The term "metalloporphyrin" used above refers to porphyrins of formula (I):

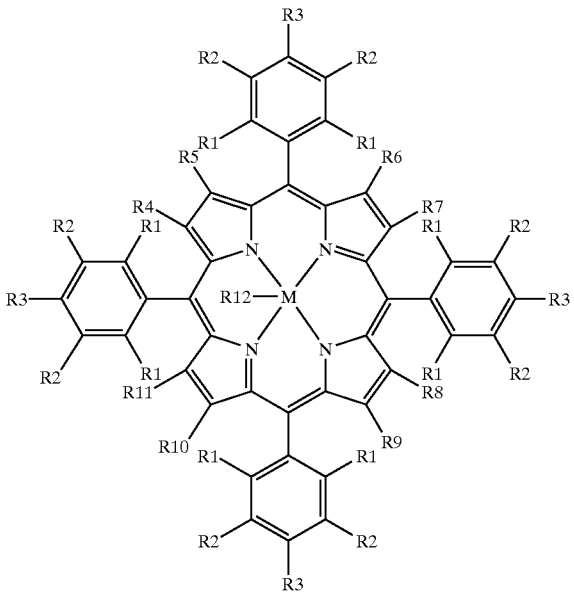

wherein

R1, R2 and R3 each independently represents a hydrogen atom or an electronegative group such as Cl, F, Br, SO3Na or an equivalent group, R4, R5; R6, R7, R8, R9, R10 and R11 each independently represents a hydrogen atom or an electronegative group such as Cl, F, Br, SO3Na or an equivalent group, R12 is Cl, acetate or an equivalent group, M is selected from the group consisting of iron, manganese, chromium, ruthenium, cobalt, copper and nickel.

Preferred metalloporphyrins include manganese (III) tetra (pentafluorophenyl)porphyrin, abbreviated herein as Mn(TPFPP)Cl, which is the compound of formula (I) above wherein M is manganese, R1, R2 and R3 are fluorine, R4, R5, R6, R7, R8, R9, R10 and R11 are hydrogen, and R12 is chlorine.

Preferred metalloporphyrins also include:

iron tetra(pentafluorophenyl)porphyrin, abbreviated herein as Fe(TPFPP)Cl, which is the compound of formula (I) above wherein M is iron, R1, R2 and R3 are fluorine, R4, R5, R6, R7, R8, R9, R10 and R11 are hydrogen and R12 is chlorine;

manganese tetra-(2,6-dichlorophenyl)porphyrin, abbreviated herein as Mn(TDCPP)Cl, which is the compound of formula (I) above wherein M is manganese, R1 is chlorine, R2, R3, R4, R5, R6, R7, R8, R9, R10 and R11 are hydrogen and R12 is chlorine;

iron tetra-(2,6-dichlorophenyl)porphyrin, abbreviated herein as Fe(TDCPP)Cl, which is the compound of formula (I) above wherein M is iron, R1 is chlorine, R2, R3, R4, R5, R6, R7, R8, R9, R10 and R11 are hydrogen and R12 is chlorine;

iron tetra-(2,6-dichlorophenyl)-octachloroporphyrin, abbreviated herein as Fe(TDCPCl$_8$P)Cl, which is the compound of formula (I) above wherein M is iron, R1 is chlorine, R2 and R3 are hydrogen, R4, R5, R6, R7, R8, R9, R10 and R11 are chlorine and R12 is chlorine;

the compound Mn((Cl$_2$Ph)$_4$(NO$_2$)P)Cl, which is the compound of formula (I) above wherein M is manganese, R1 is chlorine, R4 is NO$_2$, R2, R3, R5, R6, R7, R8, R9, R10 and R11 are hydrogen and R12 is chlorine;

the compound Mn((Cl$_2$Ph)$_4$(NO$_2$)$_2$P)Cl, which is the compound of formula (I) above wherein M is manganese, R1 is chlorine, R5 and R6 are NO$_2$, R2, R3, R4, R7, R8, R9, R10 and R11 are hydrogen and R12 is chlorine.

The amount of metalloporphyrin used ranges from 0.5 to 10% molar and is preferably 1% molar with respect to the starting material.

Temperature and Duration of the Reaction

The temperature of the reaction is between −20° C. and 100° C., and preferably between −10° C. and 40° C.

The duration of the reaction varies between a few minutes and 2 hours. Progress of the reaction can be monitored by analytical techniques such as thin-layer chromatography or HPLC. The reaction is stopped when the oxidation reaction reaches a plateau point beyond which no further conversion of the starting material is observed.

Experimental Part

Without limiting the invention, the following examples illustrate the implementation of the process of the invention.

The purity is verified by high-performance liquid chromatography (HPLC) on a Merck Lachrom instrument, and the retention time observed is reported for the eluent used.

The identity of the products obtained with the proposed structures is verified by their proton nuclear magnetic resonance and by mass spectrography.

The $^1$H NMR spectra are recorded at 400 MHz on a Brüker instrument, the compounds being dissolved in deuterochloroform, with tetramethylsilane as internal standard. The nature of the signals, their chemical shifts in ppm and the number of protons they represent are noted.

The mass spectra are recorded on a Micromass Platform LC spectrometer with positive electrospray.

EXAMPLE 1

Oxidation of N-(9-methyl-4-oxo-1-phenyl-3,4,6,7-tetrahydro-[1,4]diazepino[6,7,1-hi]indol-3-yl)-isonicotinamide (1) with 1 Equivalent of iodosobenzene (PhIO) Catalyzed by Manganese tetra-(2,6-dichlorophenyl) porphyrin Mn(TDCPP)Cl in Various Solvents These reactions in the presence of a single equivalent of iodosobenzene yield oxidation products 2, 3, 4, 5, 6 and 7 in addition to unconverted starting material, as illustrated by Scheme 1:

Scheme 1

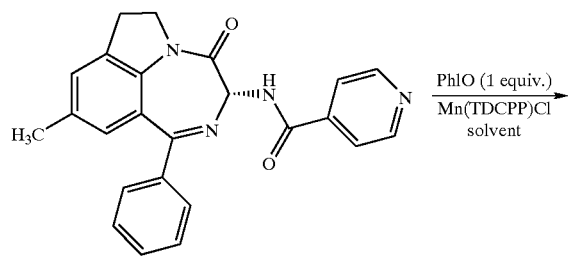

1

$\xrightarrow[\text{Mn(TDCPP)Cl}]{\text{PhIO (1 equiv.)}}$ solvent

2 + 3 + 4 + 5 + 6 + 7

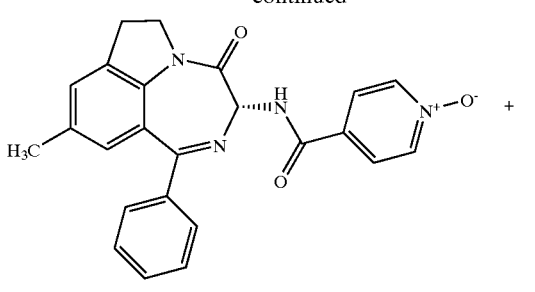

2

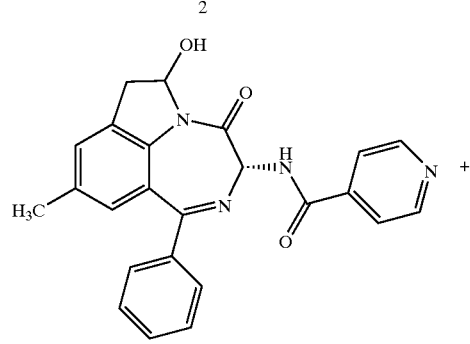

3

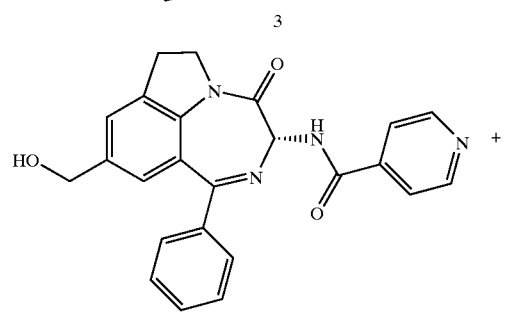

4

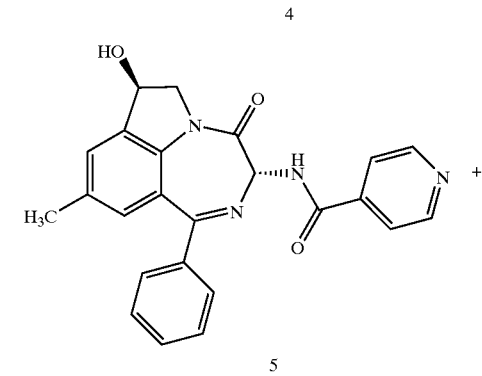

5

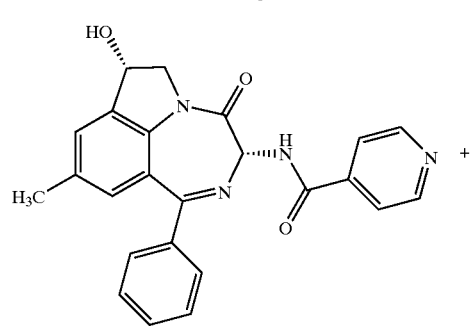

6

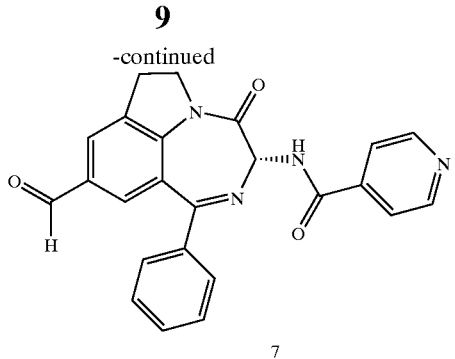

7

Compound 1 (39.6 mg, 100 μmol) is dissolved in the solvent mixture chosen (960 μL) by adding, if necessary, first the protic solvent (here used as co-solvent) and then the main solvent (dichloromethane or trifluorotoluene). The solution is stirred for 30 minutes before adding a solution of 25 mM of manganese tetra-(2,6-dichlorophenyl)porphyrin Mn(TDCPP)Cl in dichloromethane (40 μL, 1 μmol, 1 mol %). After 15 minutes iodosobenzene PhIO (22 mg, 1 equiv.) is added. One hour after the addition the reaction is monitored by analytical HPLC of a sample consisting of 10 μL of reaction mixture, 10 μL of a solution of 10 mM internal standard in 1:1 methanol/acetonitrile and 980 μL of a 1:1 solution of methanol and acetonitrile. The structure of the internal standard is as follows:

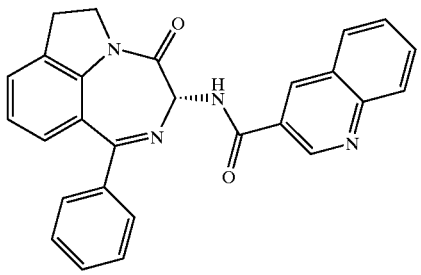

The sample is injected into a Kromasil 5C18 250×4.6 mm column and eluted at 1 mL/min with a gradient of acetonitrile and methanol in water (furnace temperature 25° C., UV 240 nm):

| min | % MeOH | % CH₃CN | % H₂O |
|---|---|---|---|
| 0 min | 15% | 15% | 70% |
| 7 min | 15% | 15% | 70% |
| 15 min | 25% | 25% | 50% |
| 35 min | 25% | 25% | 50% |
| 36 min | 0% | 25% | 75% |
| 40 min | 0% | 60% | 40% |
| 45 min | 0% | 60% | 40% |
| 50 min | 0% | 95% | 5% |
| 51 min | 15% | 15% | 70% |
| 55 min | 15% | 15% | 70% |

Under these analytical conditions the retention time of the starting material 1 is 42.7 min and that of the internal standard 44.6 min.

The products 2, 3, 4, 5, 6 and 7 formed were identified by comparing their retention times with those of the authentic products prepared by oxidation of compound 1 with 5 equivalents of hydrogen peroxide catalyzed by Mn(TDCPP)Cl in 1:1 dichloromethane/acetonitrile containing 0.8 equivalent of hexafluoroisopropanol, 1 equivalent of ammonium acetate and 0.28 equivalent of imidazole. The characteristics of these products isolated by preparative HPLC on a C18 column are as follows:

2: (This compound was also prepared by oxidation of 1 with 1 equivalent of m-chloroperbenzoic acid in dichloromethane):

HPLC=29.2 min.

$^1$H NMR (CDCl$_3$) δ (ppm) 8.1 (m, 3H), 7.8 (d, 2H), 7.4–7.3 (m, 5H), 7.2 (s, 1H), 6.9 (s, 1H), 5.5(d, 1H), 4.6 (t, 1H), 3.9 (q, 1H), 3.2 (m, 1H), 3.0(dd, 1H), 2.3 (s, 3H).

MS (ES$^+$) m/z 413 (MH$^+$)

3:

HPLC: 30.3 min.

$^1$H NMR (CDCl$_3$) δ (ppm) 8.81 (d, J=3.7 Hz, 2H), 7.93 (d, J=7.5 Hz, 1H), 7.80 (d, J=4.6 Hz, 2H), 7.57–7.39 (m, 6H), 7.35 (s, 1H), 7.09 (s, 1H), 6.33 (d, J=6.8 Hz, 1H), 5.61 (dd, J=7.6, 1.1 Hz, 1H), 3.56 (dd, J=17.4, 67 Hz, 1H), 3.05 (d, J=17.3 Hz, 1H), 2.37 (s, 3H).

MS (ES$^+$) m/z 413 (MH$^+$)

4:

HPLC: 17.7 min.

$^1$H NMR (d$_6$-DMSO) δ (ppm) 10.0 (d, 1H), 8.8 (d, 2H), 7.9 (d, 2H), 7.6–7.4 (m, 6H), 7.2 (s, 1H), 5.5 (d, 1H), 5.3 (t, 1H), 4.5 (m, 3H), 3.9 (q, 1H), 3.3 (m, 1H), 3.1 (m, 1H).

MS (ES$^+$) m/z 413 (MH$^+$)

5:

HPLC: 26.3 min.

$^1$H NMR (CDCl$_3$) δ (ppm) 8.79 (d, J=5.9 Hz, 2H), 8.02 (d, J=7.5 Hz, 1H), 7.79 (dd, J=4.5, 1.4 Hz, 2H), 7.54–7.39 (m, 6H), 7.17 (s, 1H), 5.71 (t, J=7.3 Hz, 1H), 5.58 (d, J=7.5 Hz, 1H), 4.81 (dd, J=12.3, 8.1 Hz, 1H), 3.84 (dd, J=12.3, 7.0 Hz, 1H), 2.81 (bd s, 1H), 2.39 (s, 3H).

MS (ES$^+$) m/z 413 (MH$^+$)

6:

HPLC: 24.9 min.

$^1$H NMR (CDCl$_3$) δ (ppm) 8.79 (d, J=5.9 Hz, 2H), 8.02 (d, J=7.5 Hz, 1H), 7.79 (dd, J=4.5, 1.4 Hz, 2H), 7.54–7.39 (m, 6H), 7.17 (s, 1H), 5.71 (t, J=7.73 Hz, 1H), 5.58 (d, J=7.5 Hz, 1H), 4.81 (dd, J=12.3, 8.1 Hz, 1H), 3.84 (dd, J=12.3, 7.0 Hz, 1H), 2.81 (bd s, 1H), 2.39 (s, 3H).

MS (ES$^+$) m/z 413 (MH$^+$)

7:

HPLC: 23.0 min.

$^1$H NMR (CDCl$_3$) δ (ppm) 9.90 (d, 7.9 Hz, 1H), 8.82 (d, J=5.9 Hz, 2H), 8.02–7.95 (m, 2H), 7.79 (m, 3H), 7.54–7.41 (m, 5H), 5.65 (d, J=7.6 Hz, 1H), 4.72 (m, 1H), 4.12 (dd, J=21.5, 10.2 Hz, 1H), 3.45 (m, 1H), 3.27 (dd, J=16.2, 9.7 Hz, 1H).

MS (ES$^+$) m/z 411 (MH$^+$)

The results expressed in terms of areas under the peak with respect to the internal standard are shown for different solvent systems in FIG. 1 presented in the Appendix.

These results make it possible to study the effect of the use of protic co-solvents that are good hydrogen-bond donors—such as trifluoroethanol or hexafluoroisopropanol—on the distribution of products. Thus, the presence of trifluoroethanol, or, especially, of hexafluoroisopropanol, permits decreasing the formation of product 2 originating from oxidation of the nitrogen of the pyridine of compound 1, in favor of oxidation products 3, 4, 5, 6 and 7. The latter are all the more interesting since they seem easy to prepare by conventional synthesis, in contrast to the N-oxide 2.

EXAMPLE 2

Oxidation of trans-2-[4-(1,2-diphenyl-1-butenyl)phenoxy]-N,N-dimethylamine (8) with 1 equivalent of m-chloroperbenzoic Acid (mCPBA) in Different Solvents:

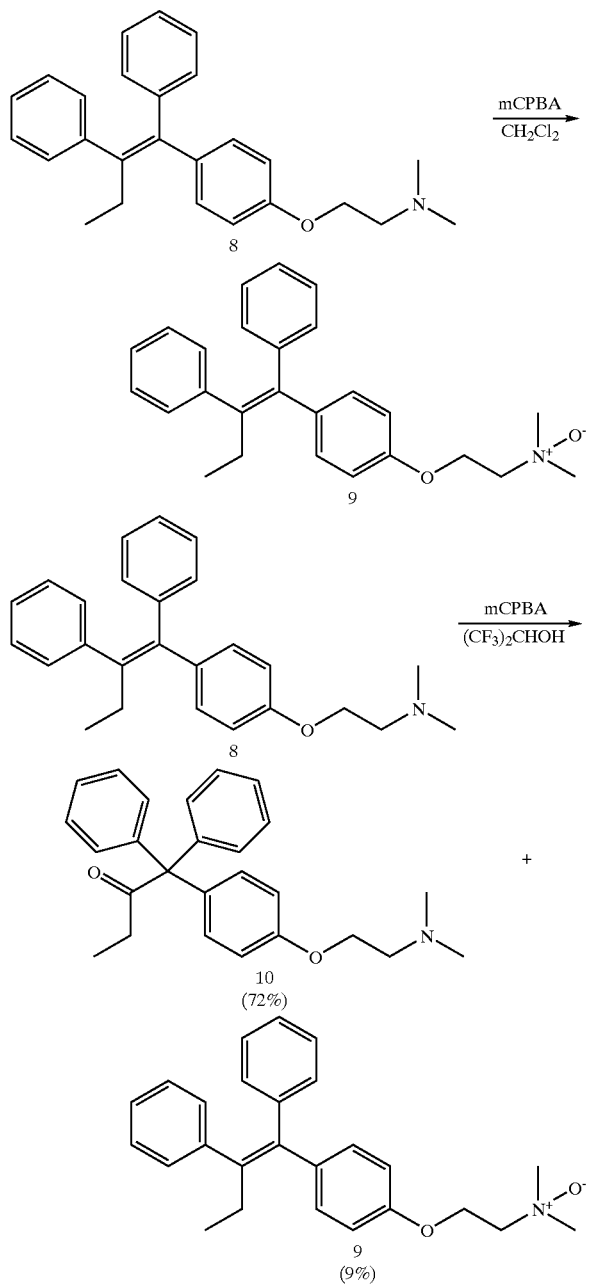

m-chloroperbenzoic acid (55 mg, 0.22 mmol, 1.1 equiv.). The solution is stirred for 2 hours. After evaporation of the solvent under reduced pressure, the crude product is purified by chromatography on a silica column, eluting with a gradient of 2 to 10% of methanol in dichloromethane, to yield 8 mg of starting material 8 (10%), 7 mg (9%) of 9 and 56 mg (72%) of 10.

9:
$^1$H NMR (CDCl$_3$) δ (ppm) 7.36–7.10 (m, 10H), 6.79 (d, J=8.7 Hz, 2H), 6.55 (d, J=8.6 Hz, 2H), 4.42 (t, J=4.0 Hz, 2H), 3.57 (d, J=4.0 Hz, 2H), 3.24 (s, 6H), 2.45 (q, J=7.4 Hz, 2H), 0.92 (t, J=7.4 Hz, 3H).
$^{13}$C NMR (CDCl$_3$) δ (ppm) 155.6, 143.6, 142.3, 141.8, 138.0, 136.5, 132.0, 129.7, 129.5, 128.1, 127.9, 127.2, 126.6, 126.1, 113.4, 70.2, 61.9, 59.9, 29.0, 13.5.
MS (ES$^+$) m/z 388 (MH$^+$)

10:
$^1$H NMR (CDCl$_3$) δ (ppm) 7.30–7.7.19 (m, 10H), 7.16 (d, J=8.9 Hz, 2H), 6.82 (d, J=8.9 Hz, 2H), 4.23 (t, J=5.1 Hz, 2H), 3.13 (d, J=5.1 Hz, 2H), 2.62 (s, 6H), 2.35 (q, J=7.3 Hz, 2H), 0.93 (t, J=7.3 Hz, 3H).
$^{13}$C NMR (CDCl$_3$) δ (ppm) 209.8, 156.7, 142.7, 135.1, 131.7, 130.3, 128.1, 126.7, 114.0, 72.4, 64.4, 56.8, 44.2, 35.0, 9.8.
MS (ES$^+$) m/z 388 (MH$^+$)

The use of a protic solvent such as hexafluoroisopropanol in the place of CH$_2$Cl$_2$ makes it possible to greatly reduce the formation of product 9, thereby promoting the formation of product 10. The properties of this protic solvent, which is a good hydrogen-bond donor, make it possible, in this case, to limit the N-oxidation of product 8 and to promote the epoxidation of a carbon-carbon double bond.

What is claimed is:

1. A process of chemoselectively oxidizing N-(9-methyl-4-oxo-1-phenyl-3,4,6,7-tetrahydro-[1,4]diazepino[6,7,1-hi]indol-3-yl-isonicotinamide having the structure:

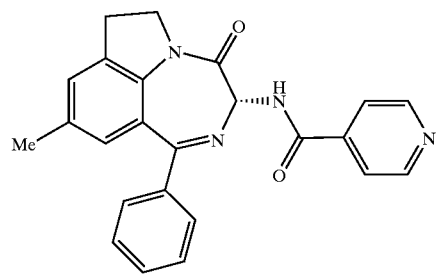

comprising contacting said organic compound with a reaction mixture comprising an oxidizing agent and a fluorinated alcohol.

2. A process according to claim 1, wherein the fluorinated alcohol is 2-fluoroethanol, 2,2,2-trifluoroethanol, 1,1,1,3,3,4,4,4-octafluorobutan-2-ol, 2,2,3,3,4,4,4-heptafluorobutan-1-ol, 2,2,3,3,3-pentafluoropropan-1-ol, 1,1,1,3,3,3-hexafluoro-2-methylpropan-2-ol or 1,1,1,3,3,3-hexafluoropropan-2-ol.

3. A process according to claim 2, wherein the fluorinated alcohol is 1,1,1,3,3,3,-hexafluoropropanol-2.

To a solution of trans-2-[4-(1,2-diphenyl-1-butenyl)phenoxy]-N,N-dimethylamine (8) (74 mg, 0.2 mmol) in dichloromethane (2 mL) is added, in portions, m-chloroperbenzoic acid (55 mg, 0.22 mmol, 1.1 equiv.). The solution is stirred for 1 hour. After evaporation of the solvent under reduced pressure, the crude product is purified by chromatography on a silica column, eluting with a gradient of 5 to 10% of methanol in dichloromethane, to yield 53 mg (69%) of white solid (9).

To a solution of trans-2-[4(1,2-diphenyl-1-butenyl)phenoxy]-N,N-dimethylamine (8, (74 mg, 0.2 mmol) in hexafluoroisopropanol (2 mL) is added, in portions,

* * * * *